(12) United States Patent
Robinson et al.

(10) Patent No.: US 7,913,534 B1
(45) Date of Patent: Mar. 29, 2011

(54) MICROFABRICATED FIELD CALIBRATION ASSEMBLY FOR ANALYTICAL INSTRUMENTS

(75) Inventors: Alex L. Robinson, Albuquerque, NM (US); Ronald P. Manginell, Albuquerque, NM (US); Matthew W. Moorman, Albuquerque, NM (US); Philip J. Rodacy, Albuquerque, NM (US); Robert J. Simonson, Cedar Crest, NM (US)

(73) Assignee: Sandia Corporation, Albuquerque, NM (US)

( * ) Notice: Subject to any disclaimer, the term of this patent is extended or adjusted under 35 U.S.C. 154(b) by 482 days.

(21) Appl. No.: 11/651,890

(22) Filed: Jan. 10, 2007

(51) Int. Cl.
*G01N 21/00* (2006.01)

(52) U.S. Cl. .................................................. 73/1.06

(58) Field of Classification Search ............. None
See application file for complete search history.

(56) References Cited

U.S. PATENT DOCUMENTS

| | | | | |
|---|---|---|---|---|
| 4,264,961 | A | * | 4/1981 | Nishimura et al. ............. 702/47 |
| 4,735,086 | A | * | 4/1988 | Follmer ....................... 73/204.19 |
| 5,792,952 | A | * | 8/1998 | Ritchart ....................... 73/204.27 |
| 6,649,909 | B2 | | 11/2003 | Russ, IV et al. |
| 6,672,129 | B1 | * | 1/2004 | Frederickson et al. ........ 73/1.06 |
| 6,797,947 | B2 | | 9/2004 | Russ, IV et al. |
| 6,997,051 | B2 | * | 2/2006 | Okazaki et al. ............. 73/204.22 |
| 7,004,423 | B2 | * | 2/2006 | Folsom et al. ................ 244/3.22 |
| 7,017,386 | B2 | * | 3/2006 | Liu et al. ......................... 73/1.03 |
| 2004/0261521 | A1 | * | 12/2004 | Hecht et al. ................. 73/204.26 |

OTHER PUBLICATIONS

Robert J. Simonson et al, "Microfabricated Chemical Source Array", U.S. Appl. No. 11/168,246, filed Jun. 27, 2005.

Anna Switaj-Zawadka et al, "Chemically Modified Glas Fiber as a Matrix-Free Reference Material for Volatile Compounds," Analytical Chemistry, vol. 77, No. 9, May 1, 2005, pp. 3018-3020.

* cited by examiner

*Primary Examiner* — Robert R Raevis
(74) *Attorney, Agent, or Firm* — Carol I. Ashby

(57) ABSTRACT

A microfabricated field calibration assembly for use in calibrating analytical instruments and sensor systems. The assembly comprises a circuit board comprising one or more resistively heatable microbridge elements, an interface device that enables addressable heating of the microbridge elements, and, in some embodiments, a means for positioning the circuit board within an inlet structure of an analytical instrument or sensor system.

18 Claims, 6 Drawing Sheets

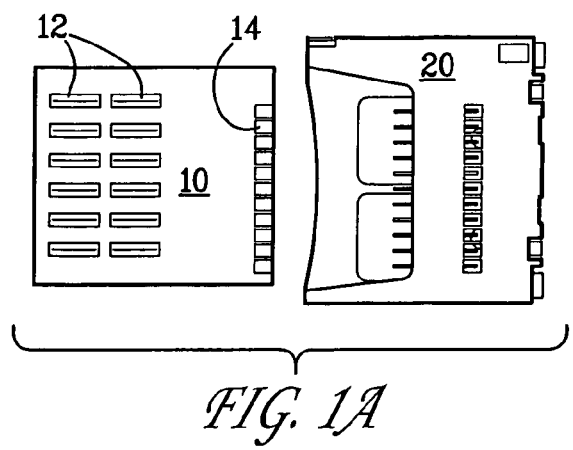
FIG. 1A
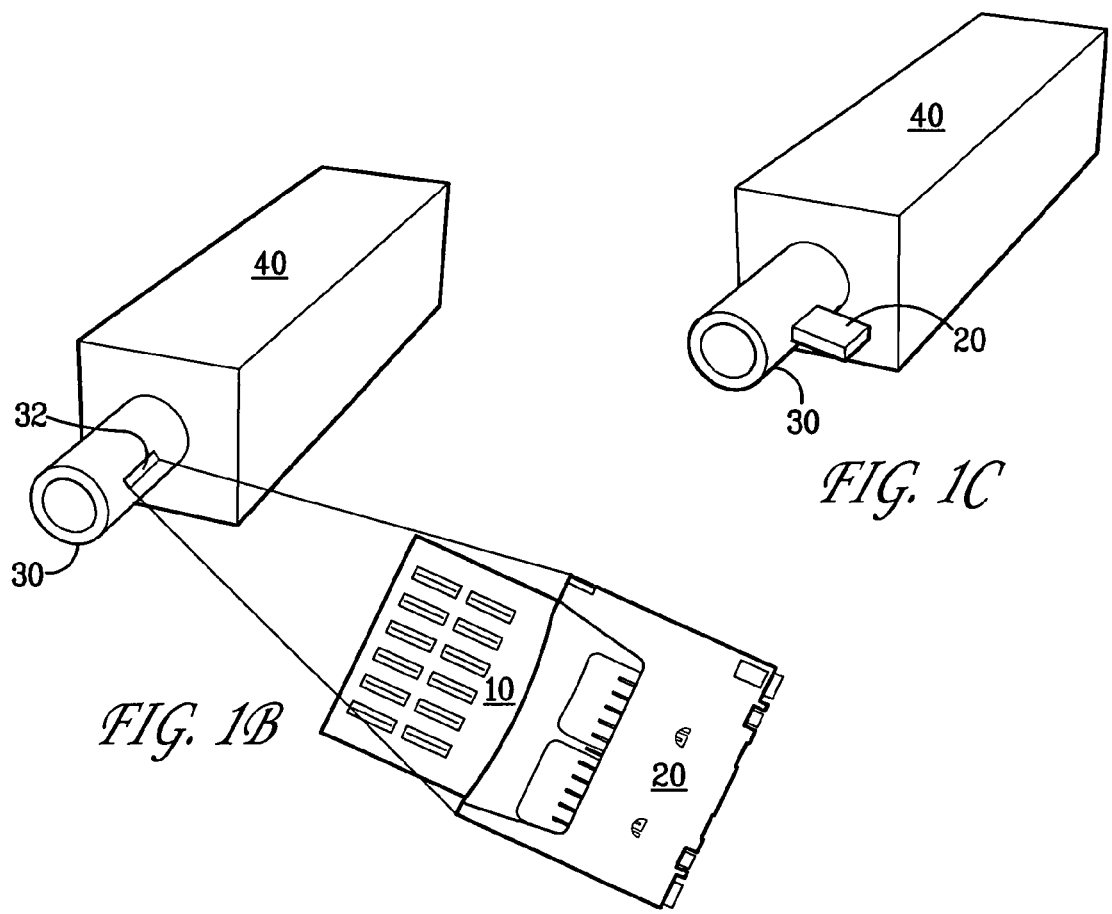
FIG. 1C
FIG. 1B

MICROFABRICATED FIELD CALIBRATION ASSEMBLY FOR ANALYTICAL INSTRUMENTS

The United States Government has rights in this invention pursuant to Department of Energy Contract No. DE-AC04-94AL85000 with Sandia Corporation.

A related U.S. patent application is application Ser. No. 11/168,246, "Microfabricated Chemical Source Array," inventors Simonson, Manginell, Robinson, Wheeler, and Trudell, filed Jun. 27, 2005 by Sandia Corporation, which is incorporated herein by reference.

BACKGROUND OF THE INVENTION

For reliable determination of the presence and/or quantity of a particular analyte, proper calibration of the analytical instrument is required. Most typical vapor-phase calibration sources that can provide a known quantity of a particular analyte vapor at an accuracy in the high part-per-trillion (ppt) range (typically on the order of 100 nanograms or so) are too complex and too large to be conveniently used in the field to calibrate remote sensors or portable analytical instruments such as small gas chromatographs, mass spectrometers, and ion mobility spectrometers. There is a need for a small, simple-to-use calibration source that can be readily employed when field-portable instruments or unattended field sensors need recalibration to ensure reliable measurements since field conditions or instrument characteristics may change.

BRIEF DESCRIPTION OF THE DRAWINGS

The accompanying drawings, which are incorporated in and form part of the specification, illustrate some embodiments of the present invention and, together with the description, serve to explain the principles of the invention.

DETAILED DESCRIPTION OF THE INVENTION

This invention comprises a microfabricated field calibration assembly for use in calibrating analytical instruments and sensor systems. For remote sensors and field analytical instruments, calibration can pose a great difficulty. While proper calibration is necessary for reliable verification of positives and for reduction of false negatives, it can be challenging to provide that calibration in the field using conventional calibration equipment such as that used in typical analytical laboratories. A field calibration assembly that can provide controlled amounts of a calibration analyte in the field without requiring return of the sensor or field instrument to a laboratory is highly desirable. By removing the need for repeated laboratory calibration, significant cost and time savings can accrue through reduced transportation costs, reduced down time, and lower laboratory equipment and personnel costs. Embodiments of this invention address this need. Additionally, automated calibration can occur in the field based on hours of operation, changing field conditions, target identification, or other calibration-triggering criteria.

Some embodiments of this present invention are designed so that the portion of the assembly that generates the vapor-phase calibration analyte is sufficiently small that it can fit in the intake port of an analytical instrument or remote sensor system. Other embodiments of the portion of the assembly that generates the vapor-phase calibration analyte can fit within the instrument housing between the inlet port and the instrument components that perform separations. The small size of various embodiments of this invention enables uses as field calibration devices for portable analytical instruments. The small size is amenable to applications using quantities down to picogram aliquots of a calibrating analyte. Embodiments of this invention are also generally suitable for application in conventional laboratory settings.

Figure 1D:
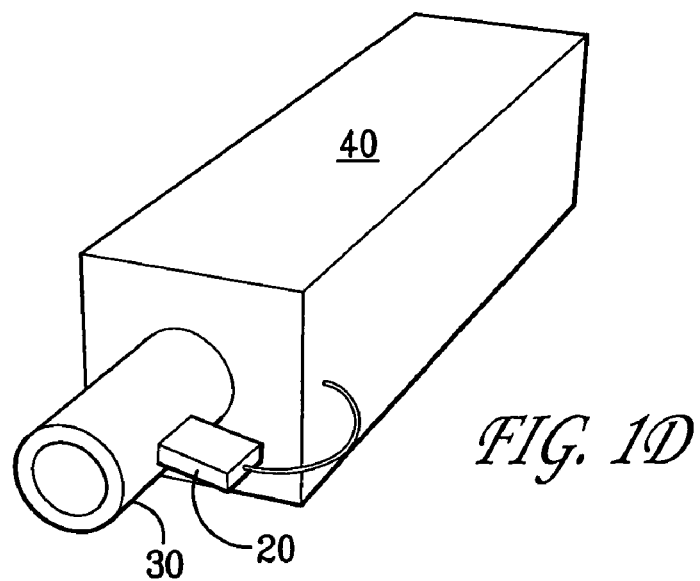
FIG. 1 illustrates an embodiment wherein a circuit board is mounted within the inlet port of an analytical instrument by means of insertion through a slit in the inlet port. The interface device remains substantially outside the inlet port in this embodiment.

The assembly comprises a circuit board comprising one or more resistively heatable microbridge elements, an interface device that enables addressable heating of the microbridge elements, and, in some embodiments, a means for positioning the circuit board within an inlet port or pre-separation region (inlet manifold) of an analytical instrument or sensor system. Addressable heating is provided by a heating source that can be selectively applied to one or more microbridge elements without heating some other microbridge elements. The assembly is also suitable for operation in free space as a source for testing collection and analysis methods of field instruments and chemical security systems, such as, for example, portal security systems. In these embodiments, the circuit-board positioning means is optional. FIG. 1 illustrates one embodiment of the invention wherein a circuit board 10 is mounted within the inlet port 30 of a portable analytical instrument 40. FIGS. 1a through 1c schematically illustrate the embodiment. The circuit board unit 10 comprises several microbridge units 12 comprising one or more microbridge elements or arrays of microbridge elements, as illustrated schematically in FIG. 1a for a circuit board unit with twelve microbridge units. The microbridge unit has a surface that is exposed to the inlet environment such that heating of a microbridge element to a calibrant-releasing temperature will release a controlled amount of calibrant material into the vapor phase within the inlet 30 of an analytical instrument 40 (FIGS. 1b and 1c). The circuit board further comprises electrical contact structures 14 that mate with electrical contact structures within an interface device 20 when the circuit board is inserted into the interface device 20. In this embodiment, the portion of the circuit board 10 containing one or more of the microbridge units 12 can be inserted into the inlet 30 by, for example, sliding the circuit board 10 into a means for positioning the circuit board, such as a mounting aperture 32 in the inlet port, resulting in an operating configuration such as that illustrated in FIG. 1c. The interface device 20 provides connection of a microbridge element to a current source that provides current for resistively heating the microbridge element. In some embodiments, the current source may be a battery contained within the interface device (FIG.

Figure 1E:
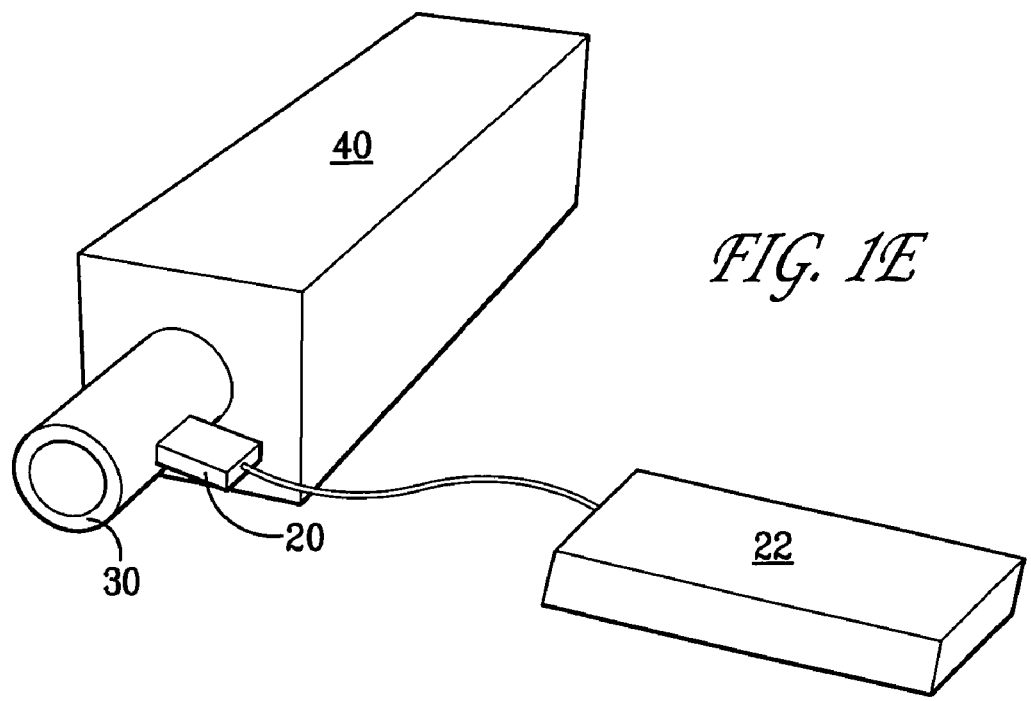

1c) or external to the interface device (FIGS. 1d and 1e) that can be selectively connected to a particular microbridge element to heat it and release the calibrant located thereon into the vapor phase. In various embodiments, selective heating of a particular microbridge element can be initiated by the analytical instrument itself (FIG. 1d) or it can be initiated by an external control means, such as, for example, a computer or a human (FIG. 1e). In some embodiments, the interface device may be connected to a current source that is integral with the analytical instrument. In some embodiments, the interface device may be connected to a current source in a module 22 that is external to the analytical instrument (FIG. 1e). In various embodiments, the heating source and the initiating signal generator can be separately located or co-located within the interface device 20, within the analytical instrument 40, or within the external module 22.

Figure 2A:
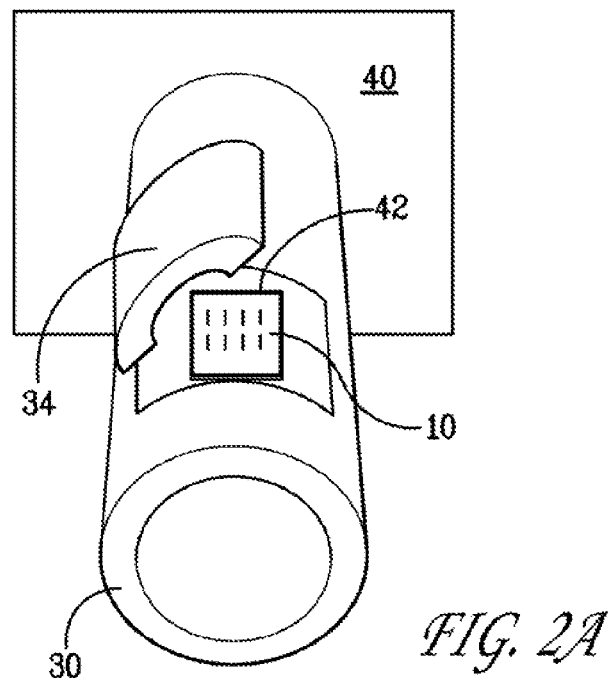
FIG. 2 illustrates some embodiments with different locations and means for positioning the circuit board within the sampling stream of an analytical instrument.
Figure 2B:
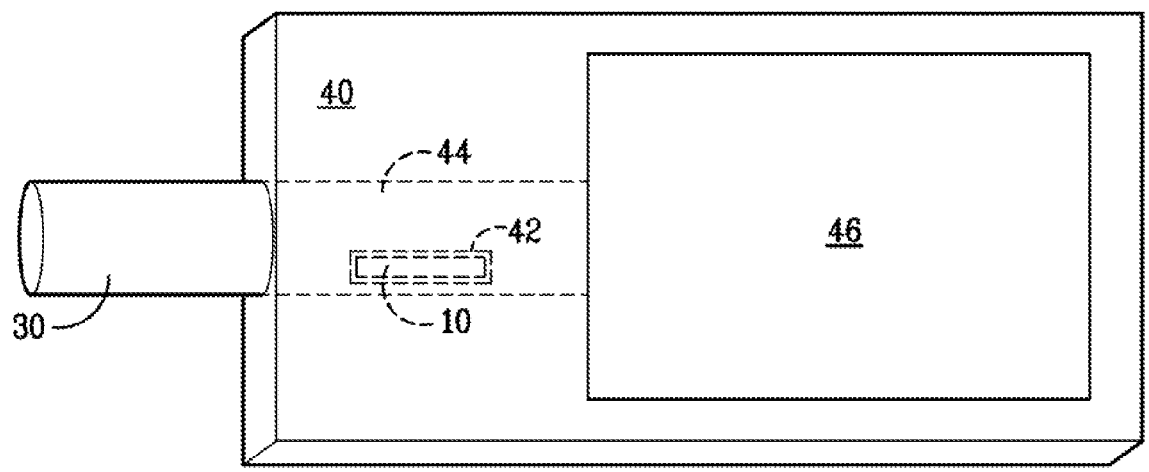
Figure 3A:
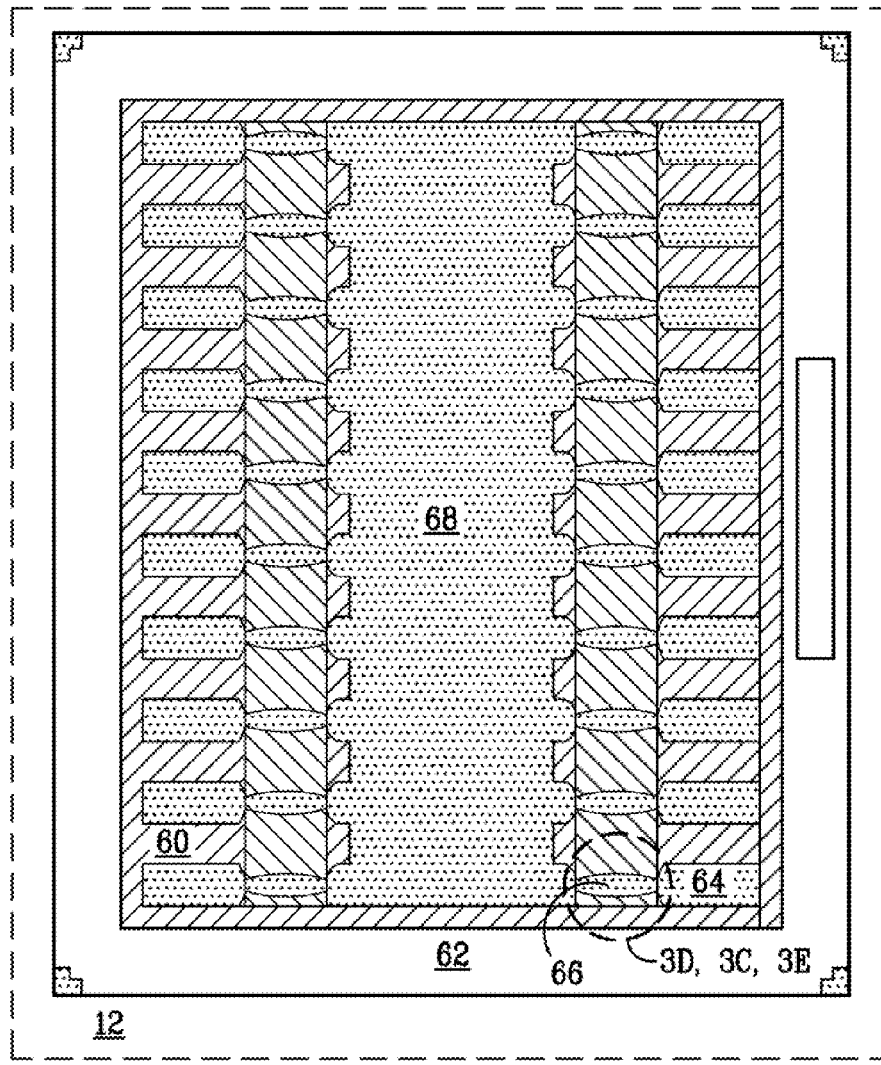
FIG. 3 illustrates a top view and a side view of an embodiment of a microbridge unit comprising an array of microbridges wherein the bridges have elongated diamond surface shapes that provide an adequate width for droplet deposition while reducing thermal conduction at the bridge ends.
Figure 3C:
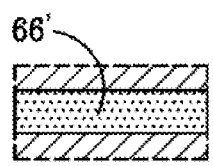
Figure 3D:
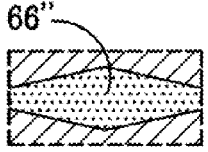
Figure 3B:
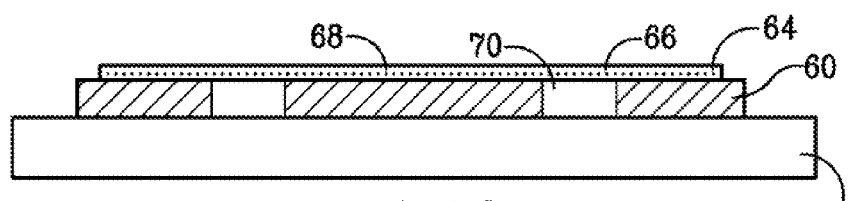
Figure 4A:
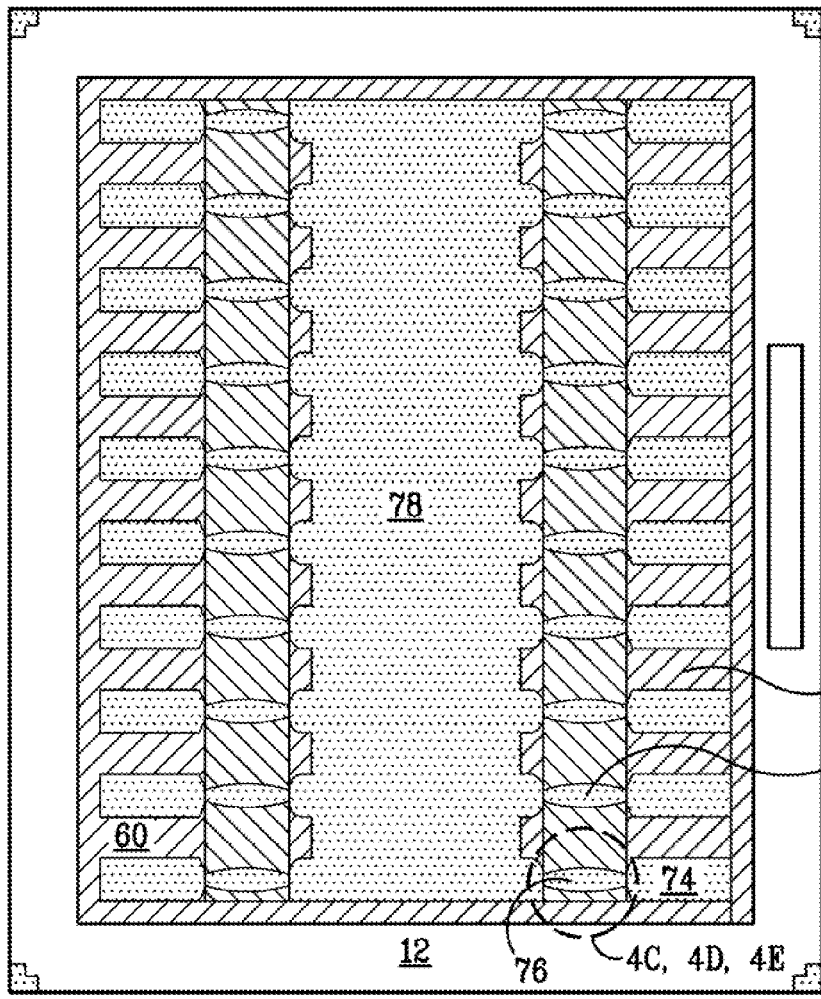
FIG. 4 illustrates a top view and a side view of a different embodiment of a microbridge unit comprising an array of microbridges wherein the bridges have elongated diamond surface shapes that provide an adequate width for droplet deposition while reducing thermal conduction at the bridge ends.
Figure 4C:
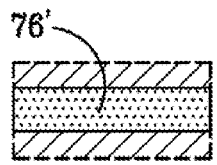
Figure 4D:
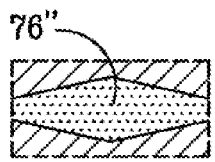
Figure 4B:
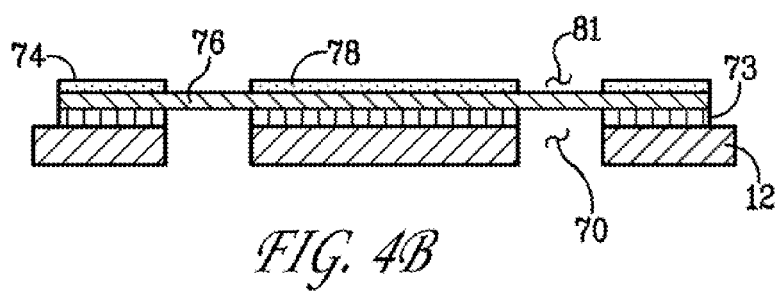

The microbridge unit can be positioned within the sample stream of the analytical instrument in a variety of ways in different embodiments of this invention. While the microbridge unit should be positioned before the separation region of the analytical instrument, there are many acceptable locations for the unit in various embodiments of the invention. For example, in some embodiments the microbridge unit can be positioned within the inlet port. The positioning can be accomplished in a number of ways in different embodiments. One example embodiment is illustrated in FIGS. 1b and 1c, where the circuit board 10 comprising the microbridge units is positioned within the inlet stream by insertion through a mounting aperture 32 such as a slit or other suitably shaped opening in the inlet port 30. The shape of the aperture is selected to mate with the shape of the circuit board or the shape of the interface device, depending upon how far the circuit board/interface device assembly is inserted into the port. In some embodiments, the microbridge unit devices on the circuit board may be mounted in sockets for easy replacement of the units, permitting reuse of the rest of the circuit board. Alternative embodiments can have the circuit board 10 mounted directly within the inlet port 30 with the circuit board being accessible through an operable lid 34 in the inlet port 30, as illustrated schematically in FIG. 2a. The circuit board in some embodiments mounts in an interface device that is integral with the inlet port. The interface device in these embodiments comprises a board socket 42. In some embodiments, the entire circuit board may be removable for replacement as needed. In some embodiments, the microbridge unit devices on the circuit board may be mounted in sockets for easy replacement of the units, permitting reuse of the rest of the circuit board. In other embodiments, the portion of the circuit board comprising the electrical connections can be positioned in a substantially fixed fashion and one or more microbridge unit devices can be replaceably mounted in one or more sockets in the circuit board through the operable lid 34, as illustrated schematically in FIG. 2a. In other embodiments, the circuit board 10 can be mounted internal to the analytical instrument instead of externally within the inlet port. One such embodiment is schematically illustrated in FIG. 2b. The varieties of means for positioning the circuit board in the inlet port can also be used for positioning the circuit board within the input manifold 44 within the analytical instrument housing 40 but before the separation region 46.

The circuit board unit 10 comprises at least one microbridge element comprising material that can be resistively heated to obtain a temperature sufficient to release a calibrant into the vapor phase. Heating of a microbridge element is the means whereby a controllable quantity of calibration analyte (calibrant) may be introduced into the vapor phase for use as a calibrant for the analytical instrument or sensor system. A wide range of materials are suitable for use in microbridge elements; many different types of materials may be employed as long as they are resistively heatable. Some examples include but are not restricted to doped silicon, polysilicon, nitride-coated silicon or polysilicon, oxide-coated silicon or polysilicon, metals, conductive polymers, and doped ceramics. Other materials may also be used as long as they can be resistively heated to a temperature that will cause the release of the calibrant into the vapor phase. Non-resistive materials with an attached resistive layer may also be used.

To minimize the energy required to selectively heat the surface upon which a calibrant is deposited, the use of a microbridge suspended over a trench can be helpful. When a surface layer with sufficiently low thermal conductivity is used that resistive heating to produce calibrant vaporization does not require excessive current and when concomitant heating of adjacent microbridges is not a problem, the microbridge may be placed directly upon the surface of the surface layer.

A range of shapes of microbridge elements can be used. The design of the microbridge element in embodiments of this invention is determined in part by the composition and quantity of calibrant that one desires to release into the analytical system or sensor system. The minimum bridge dimensions of embodiments of this invention are determined in part by such factors as the physical size of the drops of calibration solution, the physical robustness of the microbridge, and in some embodiments, the overall bridge resistance.

A range of bridge widths may be suitable for different embodiments of the invention. One factor to consider in choosing bridge width is the behavior of the calibrant solution (solution containing the calibrant or its precursors) that is being applied to the microbridge. A droplet of a calibrant solution may spread to hundreds of micrometers in diameter on a featureless surface, depending upon the droplet surface tension and the surface wettability. Bridges (microbridges) that are narrower than the expected drop diameter on a featureless substrate can be used provided the solution does not spill over or drop off the edges of the bridge. For example, surface tension at the edges of a bridge can prevent spilling over the edge, which would result in nonuniform heating of the totality of calibrant solution and consequently excessive temporal spread in the release of calibrant into the vapor phase. The surface of the bridge may be coated to repel the solution, thereby reducing spreading by changing the contact angle. Viscosity can be increased by using less solvent for a given amount of calibrant or calibrant precursor or by using different solvent combinations. If a porous absorbent is used, it can absorb the droplet and then the solvent can be evaporated. With current drop-dispensing technology that is capable of applying tens of picoliters of solution, bridges down to approximately 50 micrometer width (surface width) are suitable for some embodiments. This number may go lower if adequate control of the dispensing of smaller drops becomes possible. The upper limit of bridge width is in part dictated by the areal density of bridges that is desired. Bridges that are approximately 100 to 200 micrometers in width have been fabricated. Bridges of such widths can easily contain deposited calibration drops using currently available drop-application technology. However, wider bridges can be used in other embodiments of this invention. The upper limit on bridge width will depend in part on the ability of a bridge of a certain width and thickness to be rapidly heated to rapidly release the calibrant into the vapor phase. Release is considered to be rapid when the calibrant is released into the vapor phase during a time interval that is sufficiently short that the time of introduction of the calibrant into the separation region does not produce an unacceptable increase in the analyte peak width at the detection point of the analytical instrument.

The length of a bridge can be varied based upon considerations of mechanical strength and the number of calibrant drops that are to be used in a particular embodiment. For example, bridge length (surface length) can vary from approximately 50 micrometers to approximately 5000 micrometers. These numbers will depend upon the mechanical strength of the bridge material, with mechanically stronger materials enabling longer bridges. Longer bridges are more fragile; for many embodiments, a length of approximately 1000 micrometers provides the space for multiple independent drops of calibration solution while not being so fragile as to break easily. If the bridge length is too short, the heated region will not have good thermal isolation from the surrounding layers and substrate. In some embodiments, bridge lengths between approximately 200 and approximately 600 micrometers have been used based upon a balancing of these concerns for nitride-encapsulated polysilicon microbridges.

The bridge thickness is in part determined by the need for mechanical strength and by the desired bridge resistance. For an electrically heated bridge, the resistance is inversely proportional to the cross-sectional area and directly proportional to the length. A combination of dimensions should be chosen that creates the desired resistance, provides adequate mechanical strength, and avoids excessive thermal losses from the bridge ends. A variety of bridge shapes can be used for bridges such as 66, 66', and 66" in FIGS. 3A-D and 76, 76', and 76" in FIGS. 4A-D in various embodiments. Two examples include straight bridges with substantially rectangular surface shapes 66' and 76' and bridges with elongated diamond surface shapes 66" and 76" (substantially a parallelogram) that provide an adequate width for droplet deposition while reducing thermal conduction at the bridge ends. Other surface shapes with greater mid-bridge widths and lesser bridge-end widths include substantially ellipsoidal shapes 66 and 76 and other elongate shapes wherein the central portion of the elongate shape is wider than the end portion of the elongate shape. In other embodiments, other bridge shapes may be employed as long as they provide adequate surface area for the liquid drop, sufficient mechanical strength, suitable electrical resistance, and sufficient thermal isolation at the bridge ends. An example of another bridge shape is a meander line.

While some embodiments employ a material as the bridge that provides the suitable electrical resistance, other embodiments can use a bridge material that is not itself highly resistive, but which has one or more other desirable properties such as high thermal conductivity, easy manufacturability, or strength. A suitable resistive element can be fabricated onto the bridge when the bridge itself does not have suitable resistivity to allow heating to the desired temperature for releasing calibrant into the vapor phase.

An embodiment employing the diamond shape is illustrated in FIG. 3 for a microbridge unit 12 that comprises twenty microbridge elements. A base layer 60 is located on the surface of a substrate 62. A trench 70 is etched into the base layer 60. A patterned layer of resistive material is located on top of the base layer 60 and a microbridge 66 that is formed in the resistive material spans the trench 70. In this embodiment, an input contact 64 comprising the resistive material is connected to a return contact 68 by the microbridge 66.

Another embodiment employing the diamond shape is illustrated in FIG. 4 for a microbridge unit 12 that comprises twenty microbridge elements. The unit is made from a three layer stack of ten micron thick doped silicon 76 on ten micron thick silicon dioxide 73 on a substrate of native silicon 12. The trench 70 is etched through 12. The SiO2 layer 73 serves as an etch stop layer between 12 and 76. The bottom trench 70 is etched from the back side up to the etch stop layer. The bridges 76 and the area where the electrical contact pads 74 and 78 will be added are then photolithographically protected on the resistive layer to span the trench 70. The top trench 81 is then etched down from the top to the etch stop layer 73. The etch stop layer is then chemically removed where it is exposed in the trenches 70 and 81 and the undersides of the bridge elements 76. Metal contacts are then deposited on 74 and 78. In this embodiment, an input contact 74 comprising the resistive material is connected to a return contact 78 by the microbridge 76.

For resistively heated elements, electrical connections are made to the ends of the microbridge element so that a current may be passed through the microbridge. In many embodiments, the microbridge element is spatially separated from the main substrate to reduce the amount of current employed to raise the temperature of the microbridge element. Heating of a microbridge element is the means whereby a controllable quantity of calibration analyte or analytes may be introduced into the vapor phase for use as a calibrant for the analytical instrument or sensor system.

Figure 5:
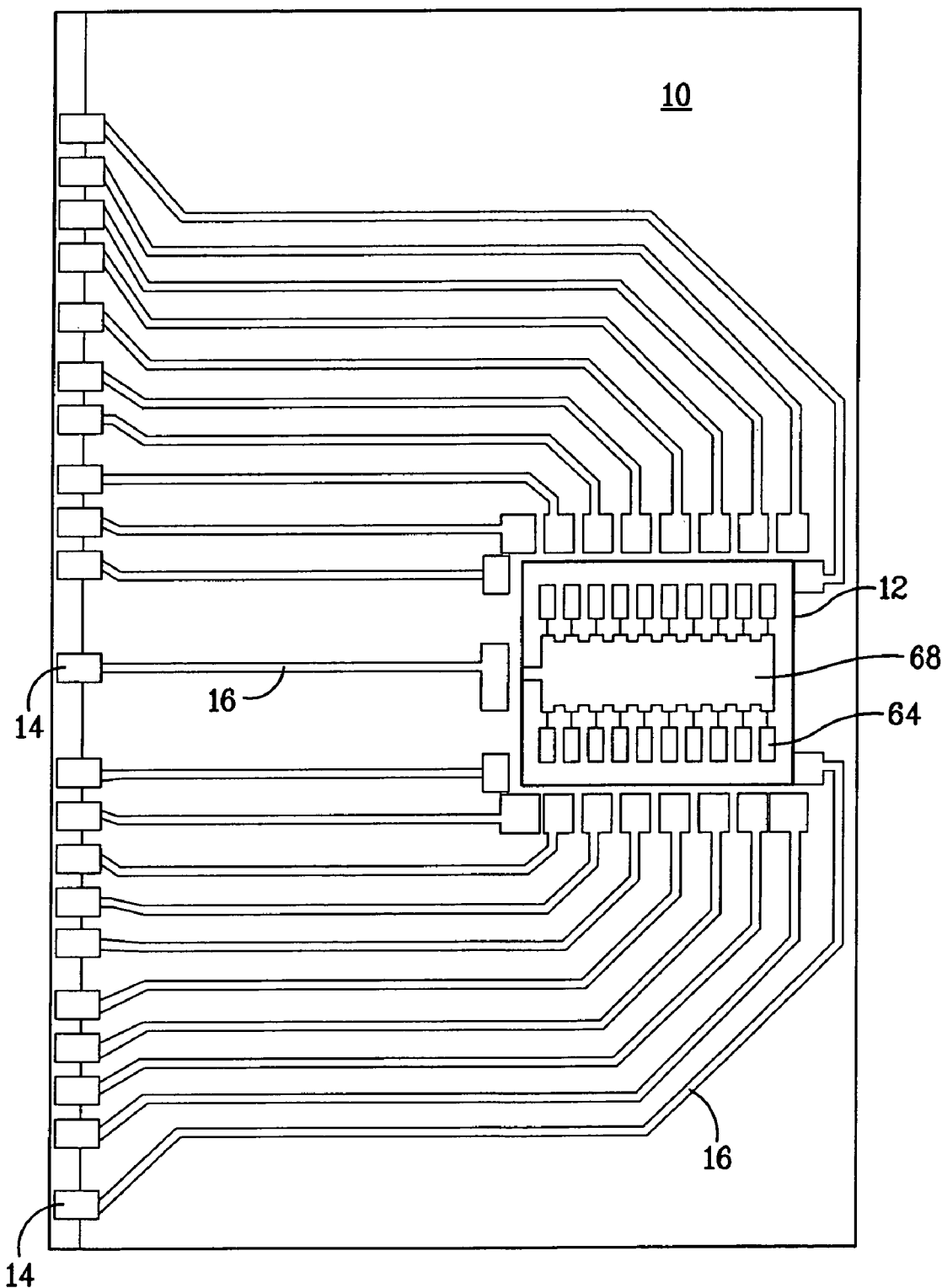
FIG. 5 illustrates an embodiment of a circuit board suitable for insertion through a slit in an inlet port. This embodiment comprises a single microbridge unit.

FIG. 5 illustrates a circuit board 10 comprising a single microbridge unit 12. This embodiment is suitable for insertion into a slit in an inlet port. The microbridge unit of this embodiment comprises 20 microbridge elements. The input contacts 64 and the return contact 68 are electrically connected to contact leads 16 on the circuit board 10. The contact leads 16 connect to electrical contact structures 14 that mate with electrical contact structures within an interface device 20 when the circuit board is inserted into the interface device 20.

The appropriate layout of electrical connections and contact structures will depend upon the mounting configuration of a particular embodiment and will be apparent to one of skill in the art.

The circuit board may comprise a single microbridge or a multiplicity of microbridges, forming a microbridge array. The microbridge elements of the microbridge array may bear deposits of the same analyte or of different analytes. The release of the calibrant (calibration analyte) may be accomplished in a number of ways. Advantageous embodiments for particular applications will depend in part on the nature of the calibrant and the manner in which the calibrant is to be released into the vapor phase. A calibrant with low vapor pressure at the typical instrument operating temperature can be deposited directly on the microbridge. An encapsulated calibrant can be deposited on the microbridge. An encapsulant is employed that does not allow the release of calibrant vapor at the normal instrument operating temperature but rather at some higher temperature; the encapsulant can thus prevent release until the encapsulated calibrant has been heated to a desired release temperature. A calibrant can be generated by the heat-activated reaction of precursors that have been deposited on the microbridge. The calibrant can either be released by thermal decomposition of a precursor to form one or more calibrant species or by the reaction of two or more precursor species to form one or more calibrant species. For example, some thermally labile organic salts are very stable below their decomposition temperatures and can serve as good calibrant precursors. A calibrant can be absorbed into or onto an absorbent matrix or adsorbent surface material. A suitable absorbent/adsorbent will have an enthalpy of absorption or adsorption that is greater than the energy provided by the ambient instrument temperature but lower than the energy provided during bridge heating.

The specific approach to releasing a calibrant by heating a microbridge will depend on the analyte and the instrument or sensor system to be calibrated; the selection of a suitable calibrant or calibrant precursor for a particular application of embodiments of this invention is within the general skill of those in the art. Selection of the appropriate approach depends in part on the calibrant and on the means for positioning the circuit board within the inlet port or inlet manifold into instrument inlet port. If it is desirable to leave the circuit board in place within the port or manifold to facilitate automated or frequent use, then a calibrant release method that involves encapsulation or absorption may be beneficial so that the finite, even if low, vapor pressure of a calibrant at normal instrument temperatures would not lead to uncharacterized loss of calibrant before heating the microbridge to trigger its controlled release.

In a particular embodiment, the microbridge unit can have one or many microbridge elements. A heating source is used to provide current to those elements of the unit that the operator wants to heat to release calibrant at a particular time. An addressable heating source allows the operator to select which elements to heat at that particular time. The heating source may be addressed directly by a human or may be computer controlled. The plurality of microbridge elements can be separately or collectively heated to deliver small aliquots of one or more desired calibrants. This may be especially desirable when interferences are a concern. It is possible to control the concentration of each calibrant by selectively heating the proper number of microbridges bearing that calibrant and by the concentration of the calibrant in the deposition solution. Multiple drops can be co-deposited to provide calibrant quantities that are multiples of those obtained from a single-drop deposition. The ability to release a calibrant for a potentially dangerous substance as minute quantities of the actual substance directly within an instrument in the field or in a laboratory instead of using a different simulant compound is an advantage of many embodiments of this invention. The ability to generate a potentially dangerous calibrant within the inlet manifold using safer precursors is also an advantage of many embodiments of this invention. With multiple microbridge elements, it is possible to have multiple calibrants readily available to select and use, depending on what is required for calibration for a particular analysis.

Some fabrication protocol for the formation of silicon microbridges are described below. In the first step of the fabrication of a silicon nitride encapsulated microbridges, a base layer of low-stress silicon nitride is deposited on a silicon substrate to a thickness of 0.8 micrometers by LPCVD (low pressure chemical vapor deposition). This layer serves to thermally and electrically isolate the microbridge from the underlying silicon substrate. It also presents a relatively non-stick surface to the finished microbridge, reducing stiction of the bridge to the substrate which can occur in the sacrificial oxide etch (release etch).

Next, 2 micrometers of silicon dioxide are deposited by LPCVD by pyrolytic oxidation of tetraethylorthosilane (TEOS). After annealing in $N_2$ for 30 min at 850° C., the film is patterned. Large openings (500×500 micrometers) are plasma etched down to the base layer of nitride, and in a completed device act as anchoring sites for the microbridge. Then 0.25 micrometer dimples are also etched into the oxide. Through the fabrication process, these dimples are converted into bosses or bushings and reduce stiction by reducing the contact area of the underside of a microbridge.

To protect the bottom surface of a polysilicon microbridge from oxidation when operated at elevated temperatures, a 0.25 micrometer layer of LPCVD silicon nitride is next deposited from TEOS. As with the first film of silicon nitride, this also acts as a stiction-reduction layer.

Deposition of polysilicon follows. Two different procedures have been used for this step. In the first, 2 micrometers of in-situ-doped polysilicon is deposited at 800 mTorr and 570° C. Doping is achieved by the addition of 1 phosphine ($PH_3$) to the silane ($SiH_4$) and carrier gas ($H_2$); n-type doping levels approaching the solid-solubility limit of P in Si (~$10^{21}$ $cm^{-3}$) are achieved.

A second method consists of three sequential depositions producing a 2.25 micrometer layer of polysilicon. The first deposition is performed at 800 mTorr and 570° C., and 0.1 micrometer of in-situ-doped polysilicon is followed by 0.05 micrometer of undoped polysilicon. Next, a 2-micrometer undoped, fine-grained layer is deposited at 580° C. Finally, 0.1 micrometer of in-situ-doped polysilicon is put down. Polysilicon produced in this fashion is known as "laminated", or "3-layer" polysilicon.

Once the polysilicon is deposited (by either method described above), a 0.3 micrometer TEOS layer is grown on top of it and eventually serves as an etching mask ("hard mask") for the polysilicon. Annealing at 1100° C. for 3 hr in a $N_2$ ambient hardens the TEOS, relieves residual stress in the polysilicon, and distributes and activates dopants. Subsequent to patterning of the hard mask, the polysilicon is dry etched to produce the desired cross-section of the microbridge.

A 0.25 micrometer layer of LPCVD silicon nitride is next deposited from TEOS. This conformal film covers the sides and top of a polysilicon microbridge and protects it from oxidation when operated at elevated temperatures. The film is dry etched to conform with the contours of the microbridge.

The final step in the fabrication sequence is the release etch, wherein the TEOS oxide layer directly below the encapsulated polysilicon bridge is removed by wet etching. Inasmuch as the oxide is "sacrificed" to produce a free-standing bridge, this step is also known as the sacrificial oxide etch. The etchant used was a 1:1 mixture of HF:HCl (49 wt % HF in $H_2O$, and 37 wt % HCl in $H_2O$) which has an etch rate of 40 micrometer/hr on annealed or densified TEOS-based silicon dioxide. The addition of HCl increases the selectivity to nitride.

As the etchant dries, capillary force draws the bridge to the substrate. After drying, van der Waal forces and hydrogen bridging can keep them stuck. Collectively, this process is known as stiction. Of course, the compliance of the microbridges in part determines whether the devices remain stuck and, indeed, whether they stick in the first place. While bridge lengths less than 200 micrometers can have limited or no stiction problems, longer devices may require special processing to reduce stiction.

The release etch was performed at both the wafer and the die level. In the former, an entire wafer (with fabricated devices) was inserted into the etchant. Individual die (containing tens of microbridges) were then separated from the wafer by either laser machining or by cleaving. Devices as long as 500 micrometers were robust enough to withstand cleaving. Most often, however, the wafer was first separated into individual die by wafer sawing, and then release etched.

The nitride encapsulation protects the polysilicon from oxidation while at elevated operating temperatures. It also can be used as protection against possible corrosive environments.

A SIMOX approach can also be used. Separation by implantation of oxygen (SIMOX) is a technique for obtaining thin layers of silicon on top of insulators. A 150-200 keV beam of $O^+$ ions is implanted into silicon to a certain depth, and at concentrations of $1-2\times10^{18}$ ions/cm$^2$, creating a SiO$_2$ layer buried below the surface of the silicon wafer. In some embodiments, the buried layer can be 2 micrometers below the surface and 0.4 micrometer in thickness. This 0.4 micrometer SiO$_2$ layer was used as the sacrificial material in much the same way that the 2 micrometer TEOS-based silicon dioxide was in the case of the polysilicon devices described previously.

To form the microbridges, the desired bridge geometry is patterned into a 0.3 micrometer TEOS hard mask formed on the SIMOX wafer surface. This pattern is then transferred to the silicon surface layer of the wafers by dry etching the unmasked regions of silicon. Etching is halted once the buried layer of SiO$_2$ is reached. Then, the hard mask is stripped and the microbridges are implanted with P$^+$ at 50 keV to a concentration of $8\times10^{15}$ ions/cm$^2$. Implanting damage is then repaired and dopants are distributed and activated by a 3 hr, N$_2$ anneal for 1100° C. Finally, the sacrificial oxide is etched in the HF/HCl mixture previously described to release the microbridges An alternate way to fabricate single-crystal silicon microbridges while still remaining in the regime of surface micromachining is through the use of "silicon on insulator" (SOI) wafers, direct bonded to silicon substrates. In such embodiments, a layered structure similar to that described for SIMOX wafers, can be produced cheaply. An SOI structure consists of a thin layer of silicon, a thin layer of oxide, and a thick layer of silicon. These layers are called the device, buried oxide, and handle layers respectively. In an SOI fabrication process, a photolithography step is used to create a soft mask which, in conjunction with dry etching, will define the bridge structures on the device layer. This dry etch will terminate on the buried oxide layer. The handle layer will be defined and etched in the same manner as the device layer, and it will serve to release the bridges. A final wet chemical etch removes the exposed buried oxide layer and completes suspension of the bridge structures. One advantage of this fabrication technique is that the bridges are suspended over holes through the entire thickness of the wafer. Lack of substrate material under the bridges removes issues such as stiction during the wet chemical release, thermal sinking of the bridges to the substrate by excess calibrant material. It also allows gas flow perpendicular to the wafer's surface during operation. Gas flow in this manner minimizes calibrant sorption onto cooler device surfaces, such as other bridges, which can maximize calibrant flowing into the analytical instrument and reduce analyte tailing.

After release etching, die containing the microbridges were affixed in 32-pin dual in-line packages (DIP) with non-conductive epoxy. The bond pads were attached to the DIP headers by wire bonding. For normal operation, Al bond wires were thermo-sonically attached directly to the heavily doped bond pads.

The circuit board comprising the microbridge unit or units can be easily removed from the interface device so that is may be replaced by another circuit board if a different calibrant is required or after the calibrants initially present on the microbridge elements of the first circuit board have been released into the vapor phase.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A field calibration assembly comprising:
a circuit board with at least one microbridge unit and electrical connections operably connected thereto;
an interface device means for connecting the electrical connections to a current source; and
a means for positioning the circuit board within an inlet structure of an analytical instrument,
wherein the microbridge unit comprises at least one microbridge element configured such that heating of the at least one microbridge element by use of the current source can provide a calibrant to the analytical instrument, and wherein the at least one microbridge element has a surface length between approximately 50 micrometers and approximately 5000 micrometers.

2. The field calibration assembly of claim 1, wherein the inlet structure is an inlet port or an inlet manifold.

3. The field calibration assembly of claim 1, wherein the current source is an addressable current source for resistively heating the at least one microbridge element of the microbridge unit.

4. The field calibration assembly of claim 1, wherein the current source is located within the interface device means, within the analytical instrument, or external to both the interface device means and the analytical instrument.

5. The field calibration assembly of claim 4, wherein the current source is a battery.

6. The field calibration assembly of claim 1, further comprising one or more calibrant deposits upon at least one of the one or more microbridge elements.

7. The field calibration assembly of claim 1, wherein a surface shape of each microbridge element is substantially a rectangle, substantially a parallelogram, substantially an ellipse, or an elongate shape wherein a central portion of the elongate shape is wider than an end portion of the elongate shape.

8. The field calibration assembly of claim 1, wherein the microbridge unit comprises one or more microbridge elements comprising a resistive material selected from n-doped silicon, p-doped silicon, polysilicon, nitride-coated silicon, nitride-coated polysilicon, oxide-coated silicon, oxide-coated polysilicon, a metal, a conductive polymer, and a doped ceramic.

9. The field calibration assembly of claim 1, wherein the microbridge unit is replaceably mounted in a microbridge unit socket on the circuit board.

10. The field calibration assembly of claim 1, wherein the interface device further comprises a means for directing that a microbridge element is to be heated.

11. The field calibration assembly of claim 1, wherein the interface device comprises a means for receiving a signal that directs that a microbridge element is to be heated.

12. The field calibration assembly of claim 11, wherein the signal that directs that the microbridge element is to be heated is provided by a signal source external to the interface device.

13. The field calibration assembly of claim 11, wherein the signal that directs that the microbridge element is to be heated is provided by the analytical instrument.

14. The field calibration assembly of claim 1, wherein the means for positioning the circuit board comprises a mounting aperture.

15. The field calibration assembly of claim 1, wherein the means for positioning the circuit board comprises a board socket.

16. The field calibration assembly of claim 1, wherein the means for positioning the circuit board is integral with the inlet structure.

17. A field calibration assembly comprising:
   a circuit board with at least one microbridge unit operably connected thereto, the at least one microbridge unit comprising at least one microbridge element, wherein the at least one microbridge element is suspended over a void;
   an interface device means for mating electrical connections of the at least one microbridge element to an addressable current source; and
   a means for directing that the microbridge element is to be heated to a temperature by an addressable heating source, wherein the microbridge unit comprising the at least one microbridge element is configured such that heating of at least one microbridge element by use of the current source can provide a calibrant to an analytical instrument, and wherein the at least one microbridge element has a surface length between approximately 50 micrometers and approximately 5000 micrometers.

18. The field calibration assembly of claim 17, further comprising one or more calibrant deposits upon at least one of the one or more microbridge elements.

* * * * *